(12) United States Patent
Dempsey (10) Patent No.: US 10,561,861 B2
(45) Date of Patent: Feb. 18, 2020

(54) VIDEOGRAPHIC DISPLAY OF REAL-TIME MEDICAL TREATMENT

(75) Inventor: James F. Dempsey, Chagrin Falls, OH (US)

(73) Assignee: VIEWRAY TECHNOLOGIES, INC., Oakwood Village, OH (US)

( * ) Notice: Subject to any disclaimer, the term of this patent is extended or adjusted under 35 U.S.C. 154(b) by 199 days.

(21) Appl. No.: 13/462,750

(22) Filed: May 2, 2012

(65) Prior Publication Data

US 2013/0296687 A1  Nov. 7, 2013

(51) Int. Cl.
*A61N 5/10* (2006.01)
*G06T 7/13* (2017.01)
(Continued)

(52) U.S. Cl.
CPC ............. *A61N 5/1067* (2013.01); *A61N 5/10* (2013.01); *A61N 5/1048* (2013.01);
(Continued)

(58) Field of Classification Search
CPC .... A61B 2019/5236; A61B 2019/5276; A61B 5/055; A61B 2019/524; A61B 8/08; A61B 2090/364; A61B 2090/374; A61B 34/30; A61B 90/36; A61B 6/4417; A61B 6/5247; A61B 6/00; A61B 5/05; A61B 5/06; A61N 7/02; A61N 2007/003; A61N 2007/0078; A61N 7/00; A61N 2007/0026; A61N 5/0601; A61N 5/062; A61N 5/0622; A61N 5/1049; A61N 2005/063; A61N 5/1067; A61N 2005/1051; A61N 5/107; A61N 5/1077; A61N 2005/1055;
A61N 2007/0039; A61N 2007/025; A61N 7/022; A61N 5/10; A61N 5/1037; A61N 5/1039; A61N 5/1042; A61N 5/1064; A61N 5/1081; A61N 2006/0612; A61N 2005/0659;
(Continued)

(56) References Cited

U.S. PATENT DOCUMENTS 3,428,307 A  2/1969  Hunter
4,019,059 A  4/1977  Brundin
(Continued)

FOREIGN PATENT DOCUMENTS

CN  1612713 A  5/2005
CN  1669599 A  9/2005
(Continued)

OTHER PUBLICATIONS

English machine translation of JP63-294839 (1998), as provided by the Japanese Patent Office.*
(Continued)

*Primary Examiner* — Amanda Lauritzen Moher
(74) *Attorney, Agent, or Firm* — Pillsbury Winthrop Shaw Pittman LLP (57) ABSTRACT

Systems and methods for creation of a videographic representation of a real-time medical treatment by a processor operating in conjunction with a treatment device and an imaging device are described. The representation may include real-time imaging data, a representation of real-time treatment data and contours of relevant anatomy among other things. Related systems and techniques are also described.

19 Claims, 6 Drawing Sheets

(51) Int. Cl.
| | |
|---|---|
| *G06T 7/00* | (2017.01) |
| *A61B 6/00* | (2006.01) |
| *G06T 7/12* | (2017.01) |
| *G06T 7/564* | (2017.01) |
| *G06T 7/50* | (2017.01) |
| *G06T 7/11* | (2017.01) |
| G06T 9/20 | (2006.01) |
| G06T 7/10 | (2017.01) |
| A61B 5/05 | (2006.01) |
| A61B 5/06 | (2006.01) |
| A61B 90/00 | (2016.01) |
| A61B 34/30 | (2016.01) |

(52) U.S. Cl.
CPC ......... *A61N 5/1049* (2013.01); *A61N 5/1071* (2013.01); *G06T 7/0012* (2013.01); *G06T 7/11* (2017.01); *G06T 7/12* (2017.01); *G06T 7/13* (2017.01); *G06T 7/50* (2017.01); *G06T 7/564* (2017.01); *A61B 5/05* (2013.01); *A61B 5/06* (2013.01); *A61B 6/00* (2013.01); *A61B 6/4417* (2013.01); *A61B 6/5247* (2013.01); *A61B 34/30* (2016.02); *A61B 90/36* (2016.02); *A61B 2090/364* (2016.02); *A61B 2090/374* (2016.02); *A61N 2005/1052* (2013.01); *A61N 2005/1055* (2013.01); *A61N 2005/1058* (2013.01); *A61N 2005/1061* (2013.01); *A61N 2005/1074* (2013.01); *G06T 7/10* (2017.01); *G06T 9/20* (2013.01); *G06T 2207/20116* (2013.01); *G06T 2207/20221* (2013.01)

(58) Field of Classification Search
CPC ...... A61N 2005/105; A61N 2007/0095; A61N 5/00; A61N 5/1048; A61N 5/1084; A61N 2005/1052; A61N 2005/1058; A61N 2005/1061; A61N 2005/1074; A61N 5/1071; G01R 33/4808; G01R 33/381; G01R 33/4812; G01R 33/3806; G21K 5/04; G06T 7/11; G06T 7/50; G06T 7/564; G06T 7/12; G06T 7/13; G06T 9/20; G06T 7/10; G06T 2207/20116; G06T 7/0012; G06T 2207/20221
USPC .......................................... 600/407, 410, 411
See application file for complete search history.

(56) References Cited

U.S. PATENT DOCUMENTS

| | | | |
|---|---|---|---|
| 4,233,662 A | 11/1980 | LeMay | |
| 4,481,657 A | 11/1984 | Larsson | |
| 4,589,126 A | 5/1986 | Augustsson | |
| 4,694,837 A | 9/1987 | Blakeley | |
| 4,771,785 A | 9/1988 | Duer | |
| 4,851,778 A | 7/1989 | Kaufman | |
| 5,027,818 A * | 7/1991 | Bova | A61N 5/10 378/65 |
| 5,039,867 A | 8/1991 | Nishihara | |
| 5,117,829 A | 6/1992 | Miller | |
| 5,216,255 A | 6/1993 | Weidlich | |
| 5,317,616 A | 5/1994 | Swerdloff | |
| 5,327,884 A | 7/1994 | Hardy | |
| 5,328,681 A | 7/1994 | Kito | |
| 5,332,908 A | 7/1994 | Weidlich | |
| 5,351,280 A | 9/1994 | Swerdloff | |
| 5,365,927 A | 11/1994 | Roemer | |
| 5,373,844 A | 12/1994 | Smith | |
| 5,377,678 A | 1/1995 | Dumoulin | |
| 5,378,989 A | 1/1995 | Barber | |
| 5,391,139 A * | 2/1995 | Edmundson | A61N 5/103 600/3 |
| 5,412,823 A | 5/1995 | Sitta | |
| 5,442,675 A | 8/1995 | Swerdloff | |
| 5,443,068 A | 8/1995 | Cline | |
| 5,458,125 A | 10/1995 | Schweikard | |
| 5,511,549 A | 4/1996 | Legg | |
| 5,513,238 A | 4/1996 | Leber | |
| 5,537,452 A | 7/1996 | Shepherd | |
| 5,538,494 A | 7/1996 | Matsuda | |
| 5,547,454 A | 8/1996 | Horn | |
| 5,555,283 A | 9/1996 | Shiu | |
| 5,596,619 A | 1/1997 | Carol | |
| 5,602,892 A | 2/1997 | Llacer | |
| 5,602,982 A | 2/1997 | Llacer | |
| 5,647,361 A | 7/1997 | Damadian | |
| 5,659,281 A | 8/1997 | Pissanetzky | |
| 5,722,411 A | 3/1998 | Suzuki | |
| 5,724,400 A | 3/1998 | Swerdloff | |
| 5,734,384 A | 3/1998 | Yanof | |
| 5,740,225 A | 4/1998 | Nabatame | |
| 5,748,700 A | 5/1998 | Shepherd | |
| 5,751,781 A | 5/1998 | Brown | |
| 5,757,881 A | 5/1998 | Hughes | |
| 5,790,996 A | 8/1998 | Narfstrom | |
| 5,802,136 A * | 9/1998 | Carol | 378/65 |
| 5,815,547 A | 9/1998 | Shepherd | |
| 5,851,182 A | 12/1998 | Sahadevan | |
| 5,894,503 A | 4/1999 | Shepherd | |
| 5,993,373 A | 11/1999 | Nonaka | |
| 6,038,283 A | 3/2000 | Carol | |
| 6,052,430 A | 4/2000 | Siochi | |
| 6,094,760 A | 8/2000 | Nonaka | |
| 6,104,779 A | 8/2000 | Shepherd | |
| 6,112,112 A | 8/2000 | Gilhuijs | |
| 6,125,335 A * | 9/2000 | Simon | G01T 1/29 250/252.1 |
| 6,144,875 A | 11/2000 | Schweikard | |
| 6,175,761 B1 | 1/2001 | Frandsen | |
| 6,198,957 B1 | 3/2001 | Green | |
| 6,207,952 B1 | 3/2001 | Kan | |
| 6,223,067 B1 | 4/2001 | Vilsmeier | |
| 6,240,162 B1 | 5/2001 | Hernandez-Guerra | |
| 6,260,005 B1 | 7/2001 | Yang | |
| 6,314,159 B1 | 11/2001 | Siochi | |
| 6,330,300 B1 | 12/2001 | Siochi | |
| 6,349,129 B1 | 2/2002 | Siochi | |
| 6,366,798 B2 * | 4/2002 | Green | 600/411 |
| 6,381,486 B1 | 4/2002 | Mistretta | |
| 6,385,286 B1 | 5/2002 | Fitchard | |
| 6,385,477 B1 | 5/2002 | Werner | |
| 6,393,096 B1 | 5/2002 | Carol | |
| 6,405,072 B1 | 6/2002 | Cosman | |
| 6,411,675 B1 | 6/2002 | Llacer | |
| 6,414,487 B1 | 7/2002 | Anand | |
| 6,422,748 B1 | 7/2002 | Shepherd | |
| 6,424,856 B1 | 7/2002 | Vilsmeier | |
| 6,466,813 B1 | 10/2002 | Shukla | |
| 6,487,435 B2 | 11/2002 | Mistretta | |
| 6,504,899 B2 | 1/2003 | Pugachev | |
| 6,512,813 B1 | 1/2003 | Krispel | |
| 6,512,942 B1 | 1/2003 | Burdette et al. | |
| 6,516,046 B1 | 2/2003 | Frohlich | |
| 6,526,123 B2 | 2/2003 | Ein-Gal | |
| 6,527,443 B1 | 3/2003 | Vilsmeier | |
| 6,542,767 B1 | 4/2003 | McNichols | |
| 6,546,073 B1 | 4/2003 | Lee | |
| 6,560,311 B1 | 5/2003 | Shepard | |
| 6,564,084 B2 | 5/2003 | Allred | |
| 6,570,475 B1 | 5/2003 | Lvovsky | |
| 6,584,174 B2 | 6/2003 | Schubert | |
| 6,594,516 B1 | 7/2003 | Steckner | |
| 6,600,810 B1 | 7/2003 | Hughes | |
| 6,609,022 B2 | 8/2003 | Vilsmeier | |
| 6,611,700 B1 | 8/2003 | Vilsmeier | |
| 6,618,467 B1 | 9/2003 | Ruchala | |
| 6,657,391 B2 | 12/2003 | Ding | |
| 6,661,870 B2 | 12/2003 | Kapatoes | |
| 6,708,054 B2 | 3/2004 | Shukla | |
| 6,719,683 B2 | 4/2004 | Frohlich | |
| 6,724,922 B1 | 4/2004 | Vilsmeier | |

(56) References Cited

U.S. PATENT DOCUMENTS

| | | | |
|---|---|---|---|
| 6,728,336 B2 | 4/2004 | Bortfeld | |
| 6,731,970 B2 | 5/2004 | Schlossbauer | |
| 6,735,277 B2 | 5/2004 | McNutt | |
| 6,757,355 B1 | 6/2004 | Siochi | |
| 6,772,002 B2 | 8/2004 | Schmidt | |
| 6,778,850 B1 | 8/2004 | Adler | |
| 6,792,074 B2 | 9/2004 | Erbel | |
| 6,849,129 B2 | 2/2005 | Bilz et al. | |
| 6,853,704 B2 | 2/2005 | Collins | |
| 6,859,660 B2 | 2/2005 | Vilsmeier | |
| 6,862,469 B2 | 3/2005 | Bucholz | |
| 6,865,253 B2 | 3/2005 | Blumhofer | |
| 6,865,411 B2 | 3/2005 | Erbel | |
| 6,879,714 B2 | 4/2005 | Hutter | |
| 6,885,886 B2 | 4/2005 | Bauch | |
| 6,891,375 B2 | 5/2005 | Goto | |
| 6,891,924 B1* | 5/2005 | Yoda | A61N 5/1031 378/65 |
| 6,898,456 B2 | 5/2005 | Erbel | |
| 6,915,005 B1 | 7/2005 | Ruchala | |
| 6,937,696 B1 | 8/2005 | Mostafavi | |
| 6,947,582 B1 | 9/2005 | Vilsmeier | |
| 6,965,847 B2 | 11/2005 | Wessol | |
| 6,980,679 B2 | 12/2005 | Jeung | |
| 6,999,555 B2 | 2/2006 | Morf | |
| 7,012,385 B1 | 3/2006 | Kulish | |
| 7,046,762 B2 | 5/2006 | Lee | |
| 7,046,765 B2 | 5/2006 | Wong | |
| 7,046,831 B2 | 5/2006 | Ruchala | |
| 7,050,845 B2 | 5/2006 | Vilsmeier | |
| 7,095,823 B2 | 8/2006 | Topolnjak | |
| 7,096,055 B1 | 8/2006 | Schweikard | |
| 7,123,758 B2 | 10/2006 | Jeung | |
| 7,130,372 B2 | 10/2006 | Kusch | |
| 7,154,991 B2 | 12/2006 | Earnst | |
| 7,162,005 B2 | 1/2007 | Bjorkholm | |
| 7,166,852 B2 | 1/2007 | Saracen | |
| 7,171,257 B2 | 1/2007 | Thomson | |
| 7,180,366 B2 | 2/2007 | Roos | |
| 7,191,100 B2 | 3/2007 | Mostafavi | |
| 7,204,640 B2 | 4/2007 | Fu | |
| 7,221,733 B1 | 5/2007 | Takai | |
| 7,227,925 B1 | 6/2007 | Mansfield | |
| 7,231,075 B2 | 6/2007 | Raghavan | |
| 7,231,076 B2 | 6/2007 | Fu | |
| 7,260,426 B2 | 8/2007 | Schweikard | |
| 7,266,175 B1 | 9/2007 | Romesberg | |
| 7,266,176 B2 | 9/2007 | Allison | |
| 7,289,599 B2 | 10/2007 | Seppi | |
| 7,298,819 B2 | 11/2007 | Dooley | |
| 7,302,038 B2 | 11/2007 | Mackie | |
| 7,315,636 B2 | 1/2008 | Kuduvalli | |
| 7,317,782 B2 | 1/2008 | Bjorkholm | |
| 7,318,805 B2 | 1/2008 | Schweikard | |
| 7,324,626 B2 | 1/2008 | Vilsmeier | |
| 7,327,865 B2 | 2/2008 | Fu | |
| 7,366,278 B2 | 4/2008 | Fu | |
| 7,394,081 B2 | 7/2008 | Okazaki | |
| 7,403,638 B2 | 7/2008 | Jeung | |
| 7,412,029 B2 | 8/2008 | Myles | |
| 7,415,095 B2 | 8/2008 | Wofford | |
| 7,423,273 B2 | 9/2008 | Clayton | |
| 7,426,318 B2 | 9/2008 | Fu | |
| 7,444,178 B2 | 10/2008 | Goldbach | |
| 7,463,823 B2 | 12/2008 | Birkenbach | |
| 7,471,813 B2 | 12/2008 | Ulmer | |
| 7,477,776 B2 | 1/2009 | Lachner | |
| 7,480,399 B2 | 1/2009 | Fu | |
| 7,505,037 B2 | 3/2009 | Wang | |
| 7,505,617 B2 | 3/2009 | Fu | |
| 7,522,779 B2 | 4/2009 | Fu | |
| 7,558,617 B2 | 7/2009 | Vilsmeier | |
| 7,570,987 B2 | 8/2009 | Raabe | |
| 7,577,474 B2 | 8/2009 | Vilsmeier | |
| 7,589,326 B2 | 9/2009 | Mollov | |
| 7,634,122 B2 | 12/2009 | Bertram | |
| 7,636,417 B2 | 12/2009 | Bjorkholm | |
| 7,638,752 B2 | 12/2009 | Partain | |
| 7,657,304 B2 | 2/2010 | Mansfield | |
| 7,688,998 B2 | 3/2010 | Tuma | |
| 7,728,311 B2 | 6/2010 | Gall | |
| 7,741,624 B1 | 6/2010 | Sahadevan | |
| 7,785,358 B2 | 8/2010 | Lach | |
| 7,901,357 B2* | 3/2011 | Boctor | A61B 8/08 600/437 |
| 7,902,530 B1 | 3/2011 | Sahadevan | |
| 7,907,987 B2* | 3/2011 | Dempsey | 600/411 |
| 7,957,507 B2 | 6/2011 | Cadman | |
| 8,139,714 B1 | 3/2012 | Sahadevan | |
| 8,190,233 B2* | 5/2012 | Dempsey | 600/411 |
| 8,214,010 B2 | 7/2012 | Courtney | |
| 8,331,531 B2 | 12/2012 | Fahrig | |
| 8,460,195 B2 | 6/2013 | Courtney | |
| 8,812,077 B2 | 8/2014 | Dempsey | |
| 8,836,332 B2 | 9/2014 | Shvartsman | |
| 8,983,573 B2 | 3/2015 | Carlone | |
| 9,114,253 B2 | 8/2015 | Dempsey | |
| 2001/0049475 A1 | 12/2001 | Bucholz | |
| 2002/0046010 A1 | 4/2002 | Wessol | |
| 2002/0087101 A1* | 7/2002 | Barrick | A61B 5/1077 600/587 |
| 2002/0091315 A1 | 7/2002 | Spetz | |
| 2002/0150207 A1 | 10/2002 | Kapatoes | |
| 2002/0151786 A1* | 10/2002 | Shukla | A61B 5/055 600/411 |
| 2002/0193685 A1* | 12/2002 | Mate et al. | 600/424 |
| 2003/0011451 A1 | 1/2003 | Katznelson | |
| 2003/0086526 A1* | 5/2003 | Clark | A61B 6/4233 378/64 |
| 2003/0112922 A1 | 6/2003 | Burdette et al. | |
| 2003/0155530 A1 | 8/2003 | Adnani | |
| 2003/0181804 A1 | 9/2003 | Gagnon | |
| 2003/0219098 A1* | 11/2003 | McNutt | A61N 5/1031 378/65 |
| 2004/0106869 A1 | 6/2004 | Tepper | |
| 2004/0254448 A1 | 12/2004 | Amies | |
| 2004/0254773 A1 | 12/2004 | Zhang | |
| 2005/0020917 A1* | 1/2005 | Scherch | A61B 8/08 600/437 |
| 2005/0053267 A1 | 3/2005 | Mostafavi | |
| 2005/0054916 A1 | 3/2005 | Mostafavi | |
| 2005/0143965 A1 | 6/2005 | Failla | |
| 2005/0197564 A1 | 9/2005 | Dempsey | |
| 2005/0201516 A1 | 9/2005 | Ruchala | |
| 2005/0254623 A1 | 11/2005 | Kamath | |
| 2006/0058636 A1 | 3/2006 | Wemple | |
| 2006/0074292 A1 | 4/2006 | Thomson | |
| 2006/0170679 A1* | 8/2006 | Wang | G06T 17/00 345/424 |
| 2006/0193441 A1 | 8/2006 | Cadman | |
| 2006/0280287 A1* | 12/2006 | Esham | A61N 5/1049 378/65 |
| 2006/0291621 A1* | 12/2006 | Yan | A61B 5/0816 378/65 |
| 2007/0003021 A1 | 1/2007 | Guertin | |
| 2007/0016014 A1 | 1/2007 | Hara | |
| 2007/0038058 A1 | 2/2007 | West et al. | |
| 2007/0043286 A1* | 2/2007 | Lu | A61N 5/103 600/407 |
| 2007/0197908 A1 | 8/2007 | Ruchala | |
| 2007/0244386 A1 | 10/2007 | Steckner | |
| 2008/0033287 A1 | 2/2008 | Schwarze et al. | |
| 2008/0093567 A1 | 4/2008 | Gall | |
| 2008/0123927 A1 | 5/2008 | Miga | |
| 2008/0177138 A1 | 7/2008 | Courtney | |
| 2008/0208036 A1 | 8/2008 | Amies | |
| 2008/0235052 A1* | 9/2008 | Node-Langlois | G06Q 50/22 705/3 |
| 2008/0303457 A1 | 12/2008 | Maltz | |
| 2009/0060130 A1 | 3/2009 | Wilkens | |
| 2009/0129545 A1 | 5/2009 | Adler | |
| 2009/0129659 A1* | 5/2009 | Deutschmann | A61N 5/1048 382/132 |

(56) References Cited

U.S. PATENT DOCUMENTS

| | | | |
|---|---|---|---|
| 2009/0149735 | A1 | 6/2009 | Fallone |
| 2009/0161826 | A1* | 6/2009 | Gertner ............... A61N 5/1017 378/65 |
| 2009/0171184 | A1 | 7/2009 | Jenkins |
| 2009/0175418 | A1* | 7/2009 | Sakurai ............... A61N 5/1048 378/98.5 |
| 2009/0264768 | A1 | 10/2009 | Courtney |
| 2010/0033186 | A1 | 2/2010 | Overweg |
| 2010/0056900 | A1 | 3/2010 | Whitcomb |
| 2010/0113911 | A1 | 5/2010 | Dempsey |
| 2010/0119032 | A1 | 5/2010 | Yan et al. |
| 2010/0239066 | A1 | 9/2010 | Fahrig |
| 2010/0312095 | A1 | 12/2010 | Jenkins |
| 2011/0012593 | A1 | 1/2011 | Shvartsman |
| 2011/0051893 | A1 | 3/2011 | McNutt |
| 2011/0118588 | A1 | 5/2011 | Komblau |
| 2011/0121832 | A1 | 5/2011 | Shvartsman |
| 2011/0218420 | A1 | 9/2011 | Carlone |
| 2011/0237859 | A1 | 9/2011 | Kuhn |
| 2011/0241684 | A1 | 10/2011 | Dempsey |
| 2011/0284757 | A1 | 11/2011 | Butuceanu |
| 2012/0022363 | A1 | 1/2012 | Dempsey |
| 2012/0070056 | A1 | 3/2012 | Krueger |
| 2012/0150017 | A1 | 6/2012 | Yamaya et al. |
| 2012/0165652 | A1 | 6/2012 | Dempsey |
| 2012/0253172 | A1 | 10/2012 | Loeffler |
| 2013/0066135 | A1 | 3/2013 | Rosa |
| 2013/0086163 | A1* | 4/2013 | Neff .................. G06Q 10/10 709/204 |
| 2013/0090549 | A1 | 4/2013 | Meltsner |
| 2013/0245425 | A1 | 9/2013 | Dempsey |
| 2013/0296687 | A1 | 11/2013 | Dempsey |
| 2013/0345556 | A1 | 12/2013 | Courtney |
| 2014/0003023 | A1 | 1/2014 | Weibler |
| 2014/0112453 | A1 | 4/2014 | Prince |
| 2014/0121495 | A1 | 5/2014 | Dempsey |
| 2014/0135615 | A1 | 5/2014 | Krulp |
| 2014/0263990 | A1 | 9/2014 | Kawrykow |
| 2014/0266206 | A1 | 9/2014 | Dempsey |
| 2014/0266208 | A1 | 9/2014 | Dempsey |
| 2014/0275963 | A1 | 9/2014 | Shvartsman |
| 2014/0330108 | A1 | 11/2014 | Dempsey |
| 2014/0336442 | A1 | 11/2014 | Keppel |
| 2014/0347053 | A1 | 11/2014 | Dempsey |
| 2015/0065860 | A1 | 3/2015 | Shvartsman |
| 2015/0077118 | A1 | 3/2015 | Shvartsman |
| 2015/0154756 | A1 | 6/2015 | Gerganov |
| 2015/0165233 | A1 | 6/2015 | Dempsey |
| 2015/0185300 | A1 | 7/2015 | Shvartsman |

FOREIGN PATENT DOCUMENTS

| | | | |
|---|---|---|---|
| CN | 1946339 | A | 4/2007 |
| CN | 101000689 | A | 7/2007 |
| CN | 101267858 | A | 9/2008 |
| CN | 101268474 | A | 9/2008 |
| CN | 101278361 | A | 10/2008 |
| CN | 101443819 | A | 5/2009 |
| CN | 102369529 | A | 3/2012 |
| CN | 102472830 | A | 5/2012 |
| CN | 102641561 | A | 8/2012 |
| DE | 3828639 | A1 | 3/1989 |
| EP | 2359905 | A1 | 8/2011 |
| EP | 2424430 | B1 | 1/2013 |
| FR | 2839894 | A1 | 11/2003 |
| GB | 2393373 | A | 3/2004 |
| JP | 63-294839 | * | 12/1998 ............... A61B 6/03 |
| JP | 2001517132 | A | 10/2001 |
| JP | 2002186676 | A | 7/2002 |
| JP | 2002522129 | A | 7/2002 |
| JP | 2005103295 | A | 4/2005 |
| JP | 2007526036 | A | 9/2007 |
| JP | 2009501043 | A | 1/2009 |
| JP | 2009511222 | A | 3/2009 |
| JP | 2009160309 | A | 7/2009 |
| JP | 2009538195 | A | 11/2009 |
| JP | 2010269067 | A | 12/2010 |
| WO | 9932189 | A1 | 7/1999 |
| WO | 02072190 | A2 | 9/2002 |
| WO | WO-03/008986 | A2 | 1/2003 |
| WO | 2004024235 | A1 | 3/2004 |
| WO | 2005081842 | A2 | 9/2005 |
| WO | 2006007277 | A2 | 1/2006 |
| WO | 2006097274 | A1 | 9/2006 |
| WO | WO-2007/007276 | A2 | 1/2007 |
| WO | 2007014106 | A2 | 2/2007 |
| WO | 2007045076 | A1 | 4/2007 |
| WO | 2007126842 | A2 | 11/2007 |
| WO | WO-2008/013598 | A2 | 1/2008 |
| WO | 2009155700 | A1 | 12/2009 |
| WO | WO-2010/103644 | A1 | 9/2010 |
| WO | 2010113050 | A2 | 10/2010 |
| WO | 2011008969 | A1 | 1/2011 |
| WO | 2012164527 | A1 | 12/2012 |

OTHER PUBLICATIONS

Hong et al. "Interventional navigation for abdominal therapy based on simultaneous use of MRI and ultrasound." *Medical and Biological Engineering and Computing*. (2006). 44(12):1127-1134.

Partial International Search Report issued in International Application No. PCT/US2013/039009, dated Oct. 18, 2013.

Lagendijk J. J. et al. "MRI guided radiotherapy: A MRI based linear accelerator." Radiotherapy & Oncology. vol. 56, No. Supplement 1. Sep. 2000. (Sep. 2000):S60-S61. XP008012866. 19th Annual Meeting of the European Society for Therapeutic Radiology and Oncology. Istanbul, Turkey. Sep. 19-23, 2000.

Batter, James M., et al. 'Accuracy of a Wireless Localization System for Radiotherapy' Int. J. Radiation Oncology Biol. Phys., vol. 61, No. 3. pp. 933-937, Nov. 1, 2004, Elsevier Inc., USA.

Baro, J et al. 'Penelope: An algorithm for Monte Carlo simulation of the penetration and energy loss of electrons and positrons in matter' Nuclear Instruments and Methods in Physics Research B 100 (1995) 31-46, Elsevier Science B.V.

Bernier, Jacques et al. 'Radiation oncology: a century of achievements' Nature Reviews—Cancer, vol. 4, Sep. 2004. pp. 737-747.

Buchanan, Roger 'Cobalt on the way out' British Medical Journal, vol. 292, Feb. 1, 1986. p. 290.

Chng, N. et al. 'Development of inverse planning and limited angle CT reconstruction for cobalt-60 tomotherapy' Proceedings of 51st Annual Meeting of Canadian Organization of Medical Physicists and the Canadian College of Physicists in Medicine, 2005, McMaster University, Hamilton Ontario. Medical Physics, 2005, pp. 2426, Abstract Only.

De Poorter J. et al. 'Noninvasive MRI Thermometry with the Proton Resonance Frequencey (PRF) Method: In Vivo Results in Human Muscle Magnetic Resonance in Medicine.' Academic Press, Duluth, vol. 33, No. 1, Jan. 1995 pp. 74-81 XP000482971.

EP App. No. 10195476.6; Extended EP Search Report dated Jul. 4, 2011.

Ep App. No. 10800553.9; Extended EP Search Report dated Oct. 17, 2013.

Extended European Search Report in European Patent Application No. EP11850577, dated Jul. 9, 2014.

Goitein, Michael. 'Organ and Tumor Motion: An Overview.' Seminars in Radiation Oncology. vol. 14, No. 1 Jan. 2004: pp. 2-9.

Goldberg, S. Nahum; G. Scott Gazelle, and Peter R. Mueller. 'Thermal Ablation Therapy for Focal Malignancy: A Unified Approach to Underlying Principles, Techniques, and Diagnostic Imaging Guidance' Amer. J. of Roentgenology, vol. 174, Feb. 2000 pp. 323-331 XP002431995.

Hajdok, George. 'An Investigation of Megavoltage Computed Tomography Using a Radioactive Cobalt-60 Gamma Ray Source for Radiation Therapy Treatment Verification.' Thesis. May 2002. 150 pages.

International Search Report and Written Opinion dated Apr. 13, 2012, for corresponding international application No. PCT/US2011/066605.

(56) References Cited

OTHER PUBLICATIONS

Jaffray, David A., et al. 'Flat-Panel Cone Beam Computed Tomography for Image-Guided Radiation Therapy' Int. J. Radiation Oncology Biol. Phys., vol. 53, No. 5, pp. 1337-1349, Apr. 3, 2002, Elsevier Science Inc., USA.

Jursinic, Paul et al. 'Characteristics of secondary electrons produced by 6, 10 and 24 MV x-ray beams' Phys. Med. Biol. 41 (1996) 1499-1509, United Kingdom.

Khan, Faiz M., 'The Physics of Radiation Therapy (second edition)', Lippincott Williams & Wilkins. Chapter 13. 1985. pp. 323-332.

Lagendijk et al, 'MRI/linac integration', Radiotherapy and Oncology, Elsevier, Ireland, (Nov. 26, 2007), vol. 86, No. 1, doi:10.1016/J.RADONC.2007.10.034, ISSN 0167-8140, pp. 25-29, XP022423061, Year 2008.

Langen, K.M. et al. 'Organ Motion and its Management.' Int J. Radiation Oncology Biol. Phys., vol. 50, No. 1, pp. 265-278. 2001. Elsevier Science Inc., USA.

Liang, J. and D. Yan. 'Reducing Uncertainties in Volumetric Image Based Deformable Organ Registration.' Medical Physics, vol. 30, No. 8, 2003, pp. 2116-2122.

Lopez, Mike R. et al. 'Relativistic Magnetron Driven by a Microsecond E-Beam Accelerator with a Ceramic Insulator' IEEE Transactions on Plasma Science vol. 32, No. 3, Jun. 2004. 10 pages.

Lurie, D.J., PhD. 'Free radical imaging' The British Journal of Radiology. 74 (2001). pp. 782-784.

Macura, Katarzyna J., MD, PhD. 'Advancements in Magnetic Resonance-Guided Robotic Interventions in the Prostate'. Top Magn Reson Imaging. vol. 19, No. 6. Dec. 2008. pp. 297-304.

Mah et al., "Measurement of intrafractional prostate motion using magnetic resonance imaging," Int. J. Radiation Oncology Boil. Phys. Vo.54, No. 2, pp. 568-575, 2002.

Medtronic, Inc.. 'Image-Guided Surgery Overview'. 2010.

Mozer, Pierre C, MD, PhD. 'Robotic Image-Guided Needle Interventions of the Prostate'. Reviews in Urology. vol. 11, No. 1. 2009. pp. 7-15.

Muntener, Michael, MD et al. 'Transperineal Prostate Intervention: Robot for fully Automated MR Imaging—System Description and Proof of Principle in a Canine Model'. Radiology. vol. 247, No. 2. May 2008. pp. 543-549.

Overweg et al. 'System for MRI guided Radiotherapy.' Proc. Intl. Soc. Mag. Reson. Med. 17(2009):594.

Patriciu, Alexandru, et al., 'Automatic Brachytherapy Seed Placement Under MRI Guidance'. IEEE Transactions on Biomedical Engineering. vol. 54, No. 8. Aug. 2007. pp. 1-8.

PCT App. No. PCT/US2010/042156; International Search Report and Written Opinion dated Sep. 10, 2010, dated Sep. 14, 2010.

Raaijmakers, A.J.E. et al. 'Integrating a MRI scanner with a 6 MV radiotherapy accelerator: dose increase at tissue-air interfaces in a lateral magnetic field due to returning electrons.' Phys. Med. Biol. 50 (2005) pp. 1363-1376.

Raaymakers, B.W. et al. 'Integrating a MRI scanner with a 6 MV radiotherapy accelerator dose deposition in a transverse magnetic field', Phys. Med. Biol. 49 (2004) 4109-4118.

Schreiner, John; Kerr, Andrew; Salomons, Greg; Dyck, Christine, and Hajdok, George, 'The Potential for Image Guided Radiation Therapy with Cobalt-60 Tomotherapy', MICCAI 2003, LNCS 2879, pp. 449-456, 2003.

Schreiner, L. John, et al. 'The role of Cobalt-60 in modem radiation therapy: Dose delivery and image guidance'. Journal of Medical Physics, vol. 34, No. 3, 2009, 133-136.

Sempau, Josep et al. 'DPM, a fast, accurate Monte Carlo code optimized for photon and electron radiotherapy treatment planning dose calculations.' Phys. Med. Biol. 45 (2000) pp. 2263-2291, Printed in the UK.

Sherouse, George W. et al. 'Virtual Simulation in the Clinical Setting: Some Practical Considerations', Int. J. Radiation Oncology Biol. Phys. vol. 19, pp. 1059-1065, Apr. 26, 1990, Pergamon Press, USA.

St. Aubin et al,, 'Magnetic decoupling on the linac in a low field biplanar linac-MR system', Med. Phys, 37 (9), Sep. 2010, pp. 4755-4761.

Stoianovici, Dan, et al. MRI Stealth Robot for Prostate Interventions. Minimally Invasive Therapy. 2007. pp. 241-248.

Tamada and Kose. 'Two-Dimensional Compressed Sensing Using the Cross-sampling Approach for Low-Field MRI Systems.' IEEE Transactions on Medical Imaging. vol. 33, No. 9. Sep. 2014. pp. 1905-1912.

Tokuda, J. et al. 'Real-Time Organ Motion Tracking and Fast Image Registration System for MRI-Guided Surgery.' Systems and Computers in Japan Scripta Technica USA. vol. 37, No. 1. Jan. 2006: 83-92. Database Inspec [Online]. The Institution of Electrical Engineers, Stevenage, GB; Jan. 2006.

Tokuda, Junichi; Morikawa, Shigehiro; Dohi, Takeyoshi; Hata, Nobuhiko; Motion Tracking in MR-Guided Liver Therapy by Using Navigator Echoes and Projection Profile Matching, 2004. vol. 11. No. 1. pp. 111-120.

Warrington, Jim et al. 'Cobalt 60 Teletherapy for Cancer. A Revived Treatment Modality for the 21st Century', 2002 The Institution of Electrical Engineers, pp. 19-1-19/19.

Wazer, David E. et al. 'Principles and Practice of Radiation Oncology (fifth edition).', Wolters Kluwer/Lippincott Williams & Wilkins. 2008. 2 pages.

Webb, S. 'The physical basis of IMRT and inverse planning' The British Journal of Radiology, 76 (2003), 678-689, 2003 The British Institute of Radiology.

Webb, Steve, 'Intensity-modulated radiation therapy using only jaws and a mask: II. A simplified concept of relocatable single-bixel attenuators', published May 22, 2002, Institute of Physics Publishing, Physics in Medicine and Biology, Phys. Med. Biol. 47 (2002) 1869-1879.

\* cited by examiner

VIDEOGRAPHIC DISPLAY OF REAL-TIME MEDICAL TREATMENT

TECHNICAL FIELD

The present disclosure relates to systems and methods for creation of a videographic representation of a real-time medical treatment performed by a treatment device in conjunction with an imaging device.

BACKGROUND

During certain medical treatments, for example, surgery or radiation therapy, movement of portions of the body being treated can decrease the effectiveness of a treatment or even cause harmful results. For example, movement of a tumor during radiation therapy can cause the radiation beam to miss the tumor and hit healthy tissue. Thus, it would be advantageous to provide visual confirmation or documentation of medical treatments, so as to enable convenient assessment of treatment accuracy.

SUMMARY

Creation of a videographic display of a real-time treatment by a treatment device operating in conjunction with an imaging device is described. An initial image of a treatment region can be obtained. One or more contours of relevant anatomy in the initial image can be provided for or calculated. Real-time images of the treatment region and real-time treatment data can be obtained during a medical treatment. One or more real-time contours of relevant anatomy in a plurality of the real-time images can be determined and a videographic display can be created. The videographic display can include the real time images, corresponding real-time contours and a representation of the real-time treatment data. Related apparatus, systems and techniques are also described.

In one aspect, real-time images of a treatment region can be obtained during a medical treatment. One or more real-time contours of relevant anatomy in a plurality of the real-time images can be determined. A videographic display of a plurality of the real-time images can be provided for. The videographic display can include the corresponding real-time contours and a representation of the real-time treatment data.

The real-time images can be obtained from a magnetic resonance imaging system and can be determined using deformable image registration. In one implementation, the medical treatment can be radiation therapy and the real time treatment data can comprise one or more of: firing status of one or more radiation beams of a radiation therapy device, location of one or more radiation beams, shape of one or more radiation beams, intensity of radiation associated with one or more radiation beams, and delivered radiation dose. The representation of the real-time treatment data in the videographic display can include one or more of: a graphical representation of a beam for one or more radiation beams when the one or more radiation beams are on, an indication of accumulated dose deposition, and textual indications of the amount of accumulated deposited dose.

Initial and real-time images can be obtained from one or more of: a magnetic resonance imaging system, a positron emission tomography scanner, a computed tomography scanner and an X-ray machine. The real-time contours can be determined using deformable image registration.

Real-time treatment data can comprise at least one of surgical instrument location information, surgical incision location information, a graphical representation of an instrument and a portion of a medical professional that can be captured in the real-time images. The videographic display can be provided on a remote device and can be three dimensional.

In another aspect, a system can comprise an imaging device, a treatment device, a display, and a processor. The imaging device can be configured to acquire real-time images of a treatment region during a medical treatment. The treatment device can be configured to acquire real-time treatment data during the medical treatment. The processor can be configured to determine real-time contours of relevant anatomy in a plurality of real-time images and to output to the display a videographic display of a plurality of the real-time images. The videographic display can include the corresponding real-time contours and a representation of the real-time treatment data.

The imaging device can be a magnetic resonance imaging system and the processor can determine the real-time contours using deformable image registration. The treatment device can be a radiation therapy device having one or more radiation beams and the real time treatment data comprising one or more of: firing status of one or more radiation beams, location of one or more radiation beams radiation beams, shape of one or more radiation beams, intensity of radiation associated with one or more radiation beams, and delivered radiation dose. The representation of the real-time treatment data in the videographic display can include one or more of: a graphical representation of a beam for one or more radiation beams when the radiation beam is on, an indication of accumulated dose deposition, and textual indications of the amount of accumulated deposited dose.

The imaging device can be selected from: a magnetic resonance imaging system, a positron emission tomography scanner, a computed tomography scanner and an X-ray machine. The system can further comprise a second imaging device that can be configured to acquire a portion of the images of the treatment region.

The processor can determine the real-time contours using deformable image registration. The real-time treatment data can comprise at least one of surgical instrument location information, surgical incision location information, a graphical representation of at least one of an instrument that is captured in the real-time images and a portion of a medical professional that is captured in real-time images. The display can be on a remote device and can be three dimensional. The videographic display can be provided over a web interface to a social media site.

These and other features, aspects, and advantages of the present disclosure will become better understood with reference to the following description and claims.

BRIEF DESCRIPTION OF DRAWINGS

Features, aspects, and implementations of the disclosure are described in conjunction with the attached drawings, in which.

DETAILED DESCRIPTION

The subject matter described herein provides many advantages, some of which are noted below. The creation of a videographic display of real-time medical treatment allows visual documentation of the treatment to be shared with a doctor, patient, family member, caretaker, etc. The viewer will be able to see, via a videographic display, portions of the body that were treated, and the operation of a treatment device acting on those body portions to treat the patient (for example, incisions by a robotic surgery scalpel, radiation by a radiation therapy device, etc.). Accordingly, the videographic display can provide evidence of whether the patient was treated properly, thereby providing information and potential psychological satisfaction to the patient or other viewers. The videographic display can also be used to educate and to assess whether additional treatments or medical-care may be required. Such real-time videographic display of treatment can also ensure efficiency amongst clinicians as their role in treatment can be recorded and shared with the patient and other individuals.

Figure 1:
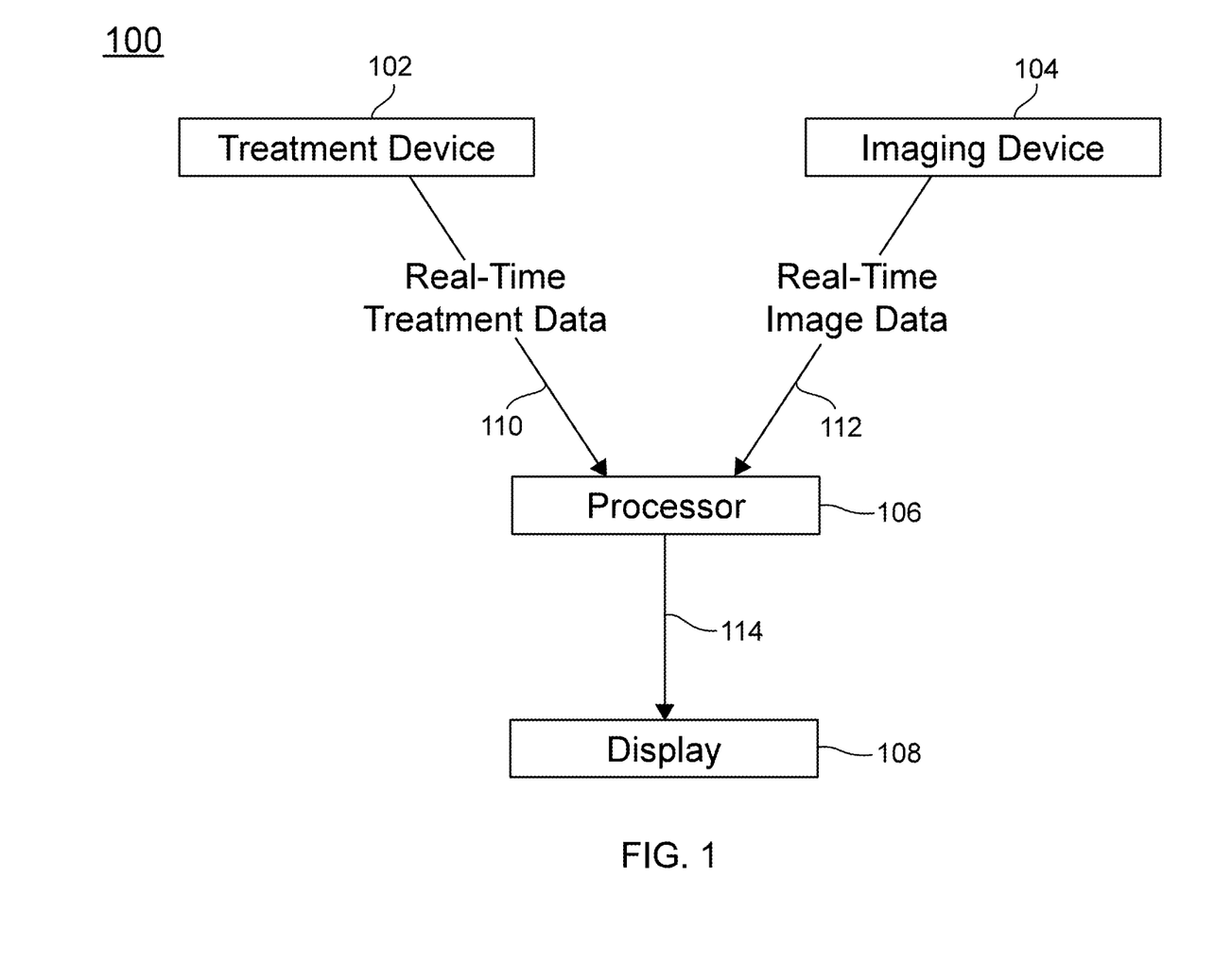
FIG. 1 is a simplified diagram illustrating aspects of a system consistent with implementations of the current subject matter.

FIG. 1 is a simplified diagram illustrating aspects of a system 100 consistent with implementations of the current subject matter. The system 100 can include at least a treatment device 102, an imaging device 104, a processor 106, and a display 108. The treatment device 102 can be a radiation therapy device, one or more robotic surgery arms, one or more surgical scalpels, or any other suitable treatment devices, for example, high intensity focused ultrasound (HIFU) ablation devices, cryo-ablation devices, laser ablation devices, RF ablation devices, and catheters or other devices for delivering treatments such as brachytherapy, stents, embolic devices, vascular grafts, suture markers, and orthopedic devices including but not limited to screws and plates. The imaging device 104 can be a magnetic resonance imaging (MRI) system, a positron emission tomography (PET) scanner, a computed tomography (CT) scanner, an X-ray machine, other imaging devices or a combination of imaging devices. The processor 106 can include a computer that includes at least one microprocessor and a machine-readable medium that can store instructions, or the processor may comprise any other computer components configured to implement the systems and methods of the present disclosure. The display 108 can include a terminal device, such as a desktop computer, laptop, tablet computer, cellular phone, television, holograph generator or any other display medium. In some implementations, the terminal device can be a remote device, remote from the treatment device 102 and the imaging device 104. Each of the arrows 110, 112, and 114 can separately characterize either a wired or wireless connection, such as cellular network, internet, local area network, or wide area network, and each connection may include multiple connections and may pass through and interact with additional elements such as servers, cloud computing devices and the like. Real-time treatment data passes over connection 110 from the treatment device 102 to the processor 106 and real-time image data passes through connection 112 from imaging device 104 to processor 106. Information required to create a videographic display travels across connection 114 from the processor 106 to the display 108.

Figure 2:
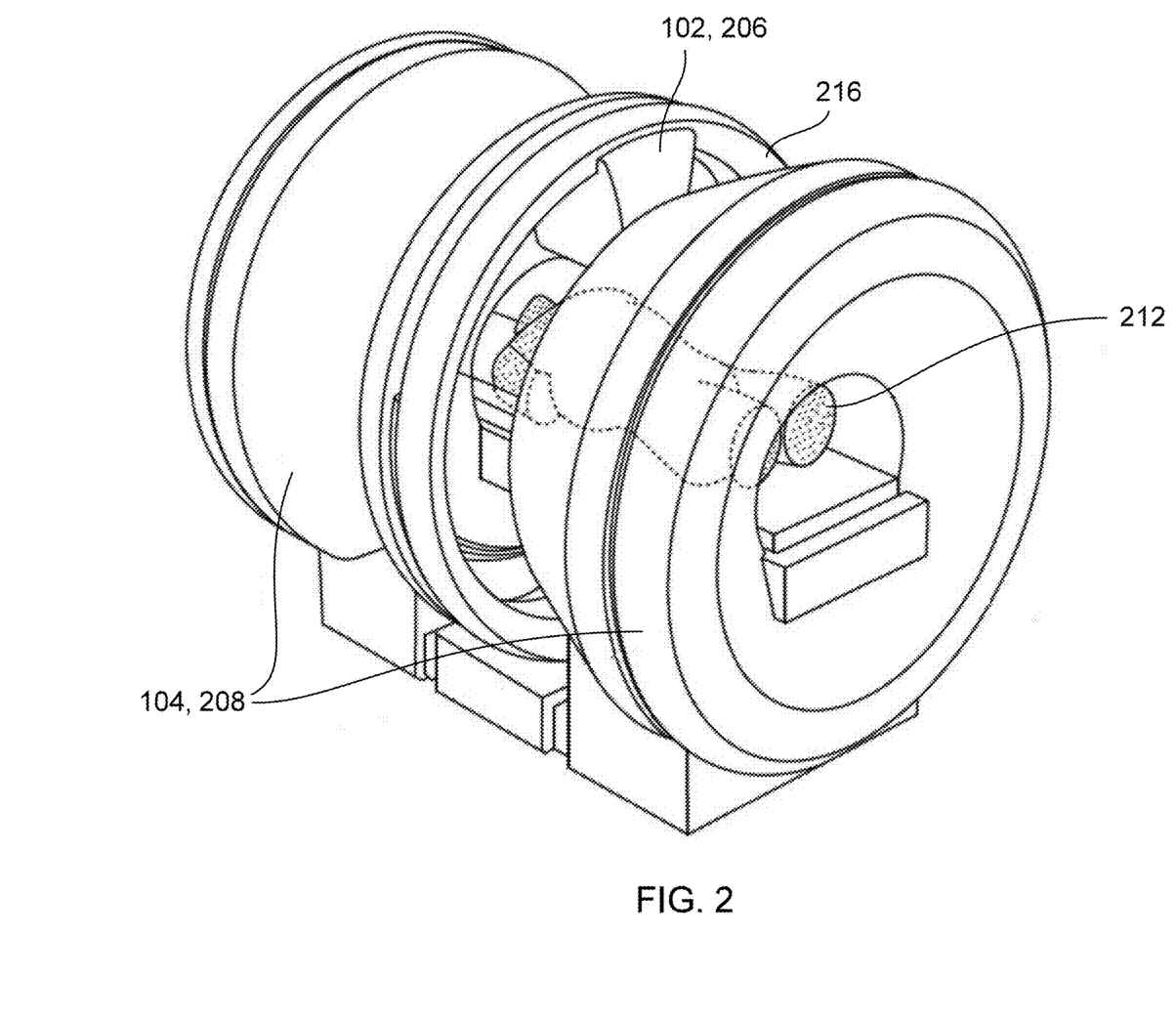
FIG. 2 illustrates an example of a treatment device operating in conjunction with an exemplary imaging device.

FIG. 2 illustrates an example of a treatment device 102 operating in conjunction with an imaging device 104 as described in the present disclosure. The treatment device 102 in this example is a radiation therapy device 206 mounted on a rotatable gantry 216. The imaging device 104 in this example is a magnetic resonance imaging (MRI) system 208. Radiation therapy device 206 can include one or more radiation beam sources, such as a cobalt-60 source or a linear accelerator, which can be controlled to transmit radiation to a predetermined anatomy of a patient 212. The radiation therapy device 206 can further include one or more multi-leaf collimators to shape the radiation beams transmitted to patient 212. The radiation beam or beams may thus be turned on and off, can be rotated on the gantry 116, and can have their shape and intensity modified by multi-leaf collimators or other devices.

Figure 3:
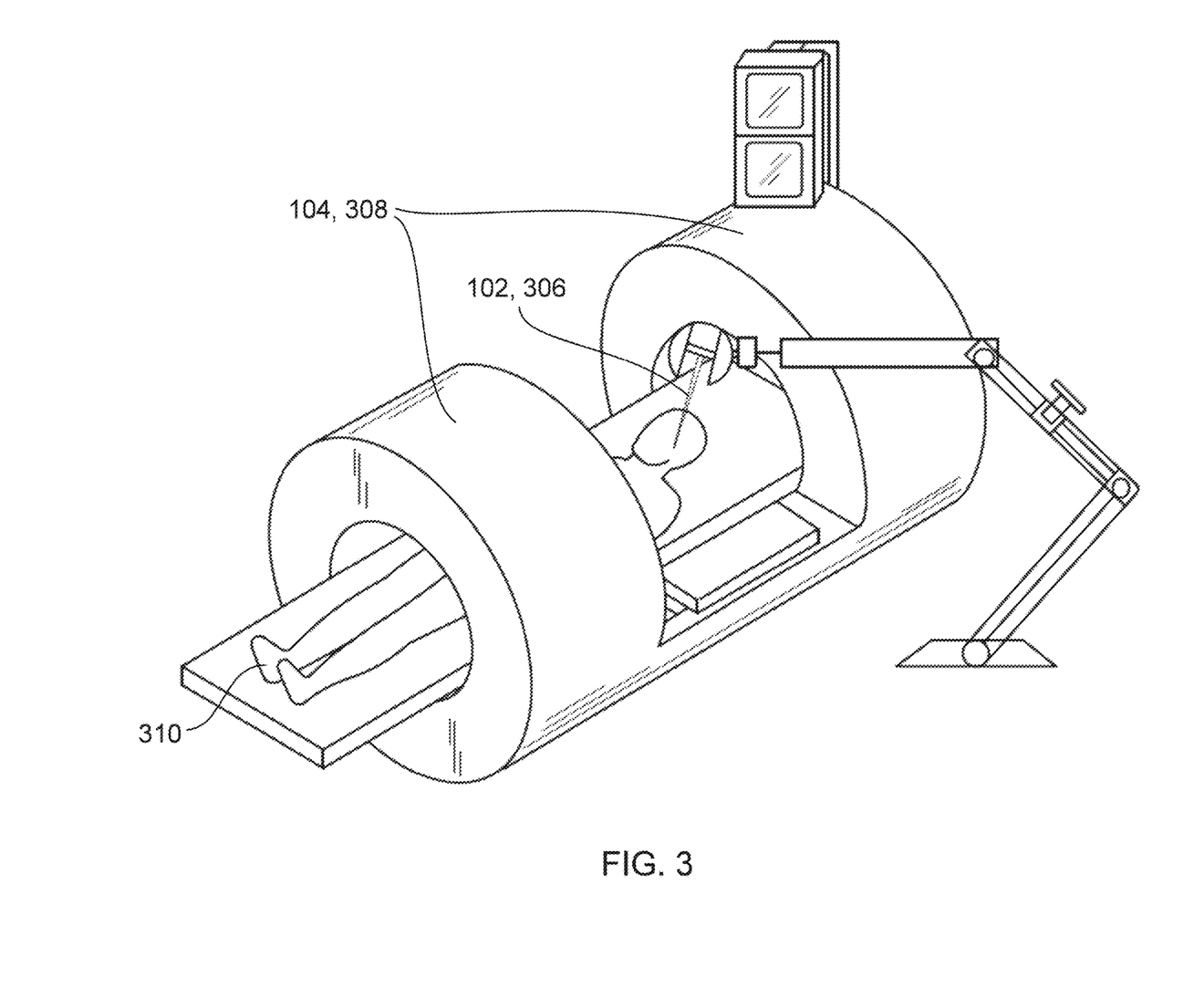
FIG. 3 illustrates another example treatment device operating in conjunction with an exemplary imaging device.

FIG. 3 illustrates an additional example of a treatment device 102 operating in conjunction with an imaging device 104 as described in the present disclosure. The treatment device 102 in this example is a robotic surgery device 306. The imaging device 104 in this example is a magnetic resonance imaging (MRI) system 308. The robotic surgery device 306 can be controlled to move with respect to the body of a patient 310 so as to operate on the patient 310.

Figure 4:
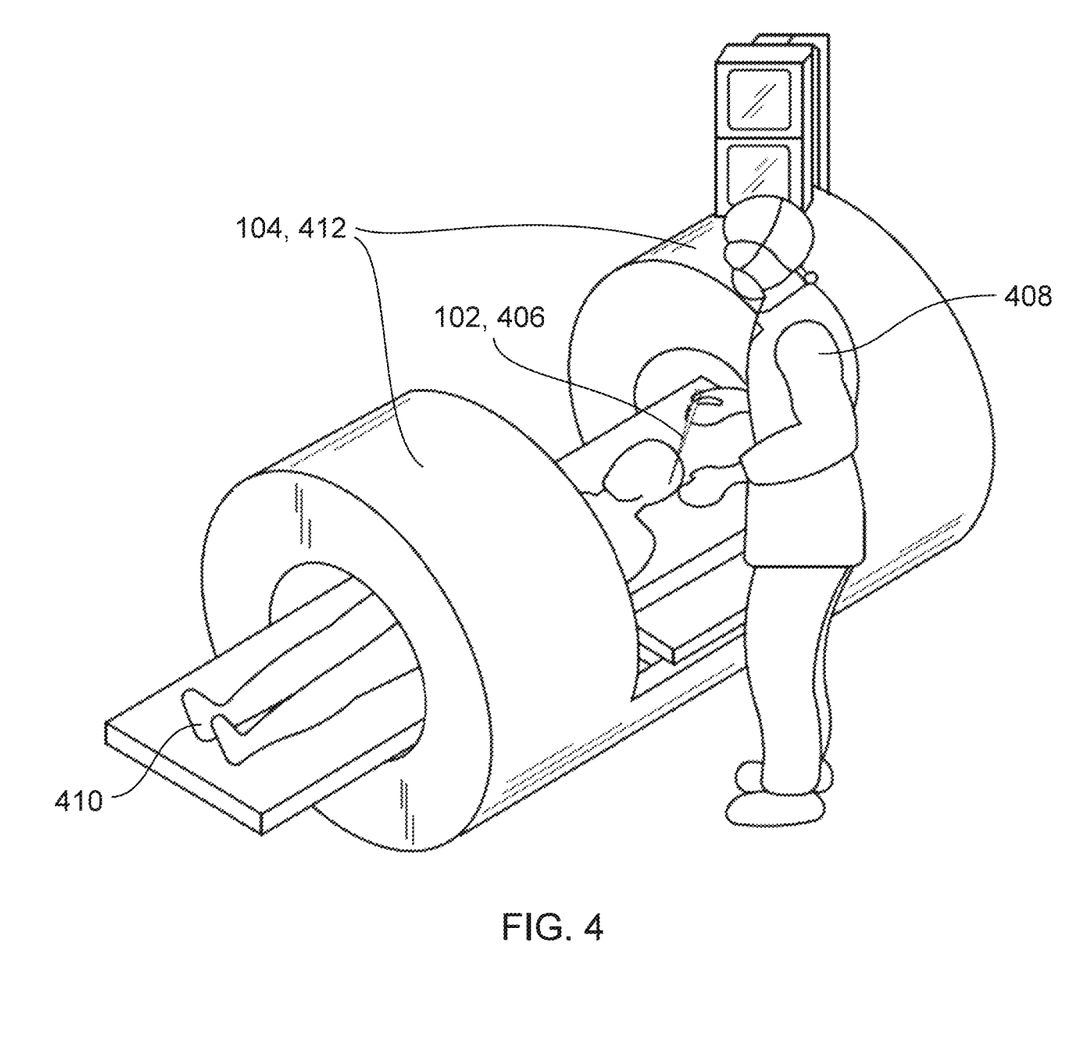
FIG. 4 illustrates yet another example of treatment device operating in conjunction with an imaging device.

FIG. 4 illustrates an additional example of a treatment device 102 operating in conjunction with an imaging device 104 as described in the present disclosure. The treatment device 102 in this example is a surgical scalpel 406. The imaging device 104 in this example is a magnetic resonance imaging (MRI) system 412. Surgical scalpel 406 can be configured to be used by a clinician 408 on a portion of the body of patient 410 to perform a surgical procedure.

Further details regarding the exemplary implementations of FIGS. 2-4 will be understood with reference to the below explanation of an exemplary method of the present disclosure.

Figure 5:
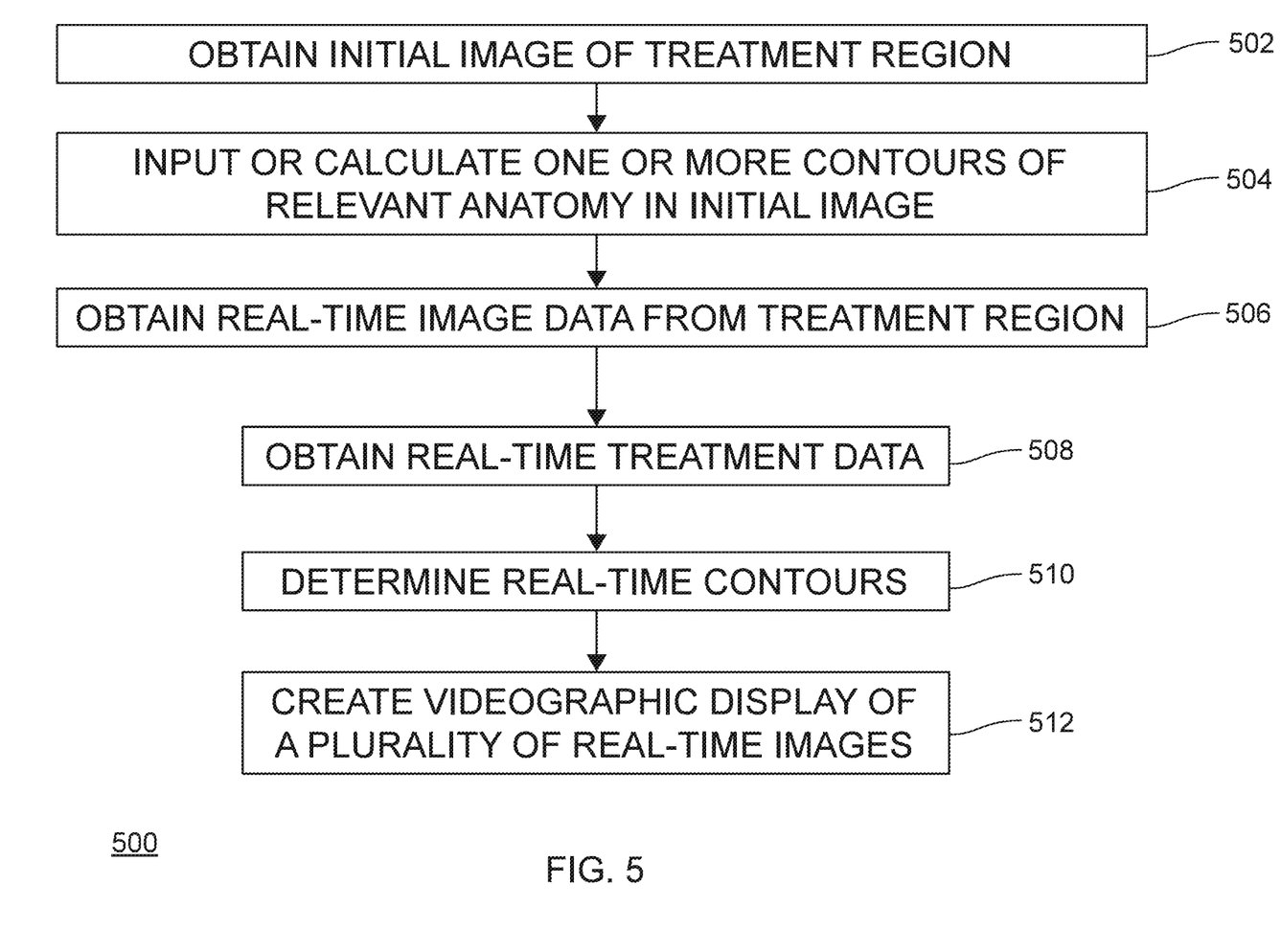
FIG. 5 is a simplified diagram illustrating aspects of a method consistent with implementations of the current subject matter.

FIG. 5 is a simplified diagram illustrating aspects of an exemplary process 500 that may be used to implement the method of the present disclosure. For example, an initial image of a treatment region may be obtained from imaging device 104 at 502. One or more contours of relevant anatomy may then be provided or calculated in the initial image at 504. As an example, contours may include the boundaries of a tumor to be treated and also the boundaries of nearby anatomy that must be avoided in the treatment. These contours may be developed manually by a clinician. In an alternate implementation, the contours can be developed using automated computer programs.

After the medical treatment begins, real-time image data from the treatment region can be obtained using imaging device 104 at 506. Additionally, real-time treatment data can be obtained from treatment device 102 at 508.

Real-time treatment data for the implementation depicted in FIG. 2 (wherein treatment device 102 is a radiation therapy device 206) may include one or more of: the firing status of the one or more radiation beams, the angular location of the beam(s), the shape of the beam(s), the intensity of radiation associated with the beam(s), the delivered radiation dose, and the like. Such treatment data can be acquired through, for example, sensors associated with the radiation source, the rotatable gantry, the leaves on the multi-leaf collimator(s), and the control system of the radiation therapy device. Treatment data could also be gathered from the imaging device 102 itself. Other data could be gathered as well, as would be understood by those skilled in the art.

Real-time treatment data for the implementation depicted in FIG. 3 (wherein treatment device 102 is a robotic surgery device 306) may include one or more of: the location and trajectory of the robotic surgery device 306, coordinates (for example, Cartesian coordinates, spherical coordinates, or cylindrical coordinates) of the incision into the body of the patient 310, the shape of the operative implement of robotic surgery device 306, audio and/or visual recordings of one or more clinicians involved in the surgery, and the like. Such treatment data can be acquired through, for example, sensors associated with the robotic surgery device 306 to record its trajectory, location or change in shape or a graphic or videographic camera or other imaging modality used in conjunction with the robotic surgery device 306. Treatment data could also be gathered from the imaging device 102 as well. Other data could be gathered as well, as would be understood by those skilled in the art.

Real-time treatment data for the implementation depicted in FIG. 4 (wherein treatment device 102 is a surgical scalpel 406) may include one or more of: the location and trajectory of the surgical scalpel 406, coordinates (for example, Cartesian coordinates, spherical coordinates, or cylindrical coordinates) of the incision into the body of the patient 416, audio and/or visual recordings of one or more clinicians involved in the surgery, and the like. Such treatment data can be acquired through, for example, sensors associated with the surgical scalpel 406 to record its trajectory or location or a graphic or videographic camera or other imaging modality used in conjunction with the surgical scalpel 406. Treatment data could also be gathered from the imaging device 102 as well. Other data could be gathered as well, as would be understood by those skilled in the art.

At 510 in FIG. 5, real-time contours of the relevant anatomy in the real-time images may be determined. The real-time contours can be determined using deformable image registration and the initial image and contours acquired in 502 and 504, as well as with real-time images and contours. Contours may also be developed using other image processing techniques individually or in combination, such as, edge detection, pattern recognition, and the like.

A videographic display of a plurality of the real-time images can be created at 512 in FIG. 5. The display can include the corresponding real-time contours of the plurality of the real-time images and a representation of the real-time treatment data. Display 108 may be a terminal device, such as a desktop computer, laptop, tablet computer, cellular phone, television, holograph generator or any device capable of displaying a video. The display 108 may be located with the treatment device 102 and imaging device 104 or it may be remote from that location. As previously mentioned, the videographic display may utilize a wired connection or a wireless connection, such as cellular network, internet, local area network, wide area network, metropolitan area network, Bluetooth network, infrared network, Zigbee wireless network, Wibree network, and the like, and each connection may include multiple connections and may pass through and interact with additional elements such as servers and cloud computing devices. In one example, the videographic display may be provided over a web interface to a site such as a social media site where individuals can post, share and comment on various documented medical treatments.

In one implementation, the components of the treatment data and image data can be assembled together at the processor 106 such that a videographic file can be sent to display 108. In an alternate implementation, the components of the treatment data and image data can be sent separately from the processor 106 to display 108 where the separately received components can be assembled to form the videographic display. The assembly can be performed based upon selections by a viewer of the videographic display.

In one implementation, acquired treatment data can be overlaid on respective real-time images to form a set of final images, and then images of the set can be combined to form the videographic display. This overlaying can be performed using a correlation, in time and space, of treatment data and corresponding image data.

At least a portion (for example, a predetermined number) of images of the set of final image data may be combined to form the videographic display. The predetermined number can vary depending factors such as, the communication channel utilized (for example, direct wire connection, cellular network, internet, local area network, wide area network, metropolitan area network, Bluetooth network, etc.), the available bandwidth of the communication channel, the display type (for example, laptop, desktop computer, tablet computer, cellular phone, wireless device) and other factors. In one example, the predetermined number when the display 108 is a mobile phone can be lower than the predetermined number when the display 108 is a high processing capability computer. In some implementations, the predetermined number can be determined by a clinician based on a personal preference of the clinician or the patient.

Figure 6:
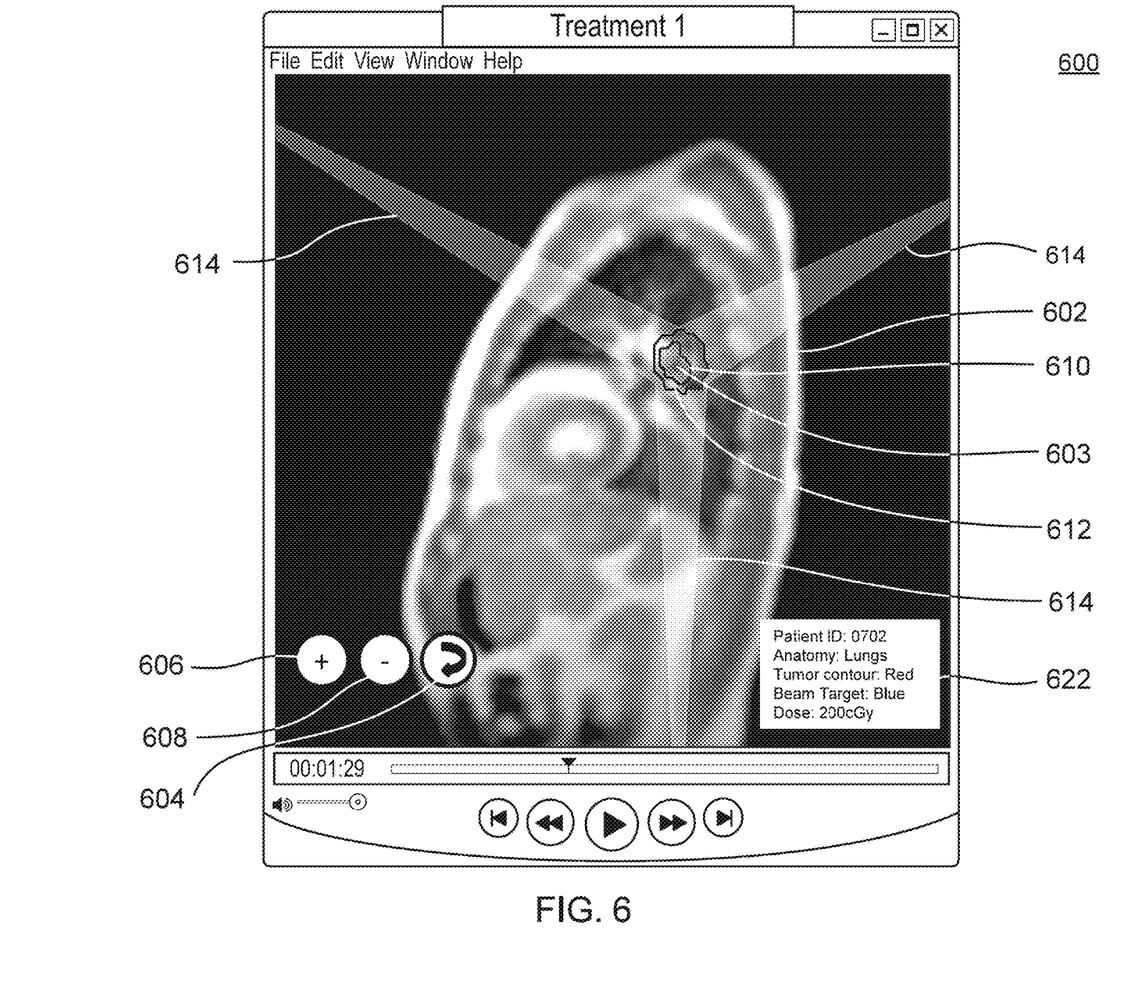
FIG. 6 illustrates a videographic display consistent with implementations of the current subject matter.

FIG. 6 illustrates one example of a videographic display 600 that can be created utilizing the method of the present disclosure and the particular treatment device of a radiation therapy device. It is understood that numerous other types of displays can be created based upon the teachings herein. The videographic display 600 can include a graphic or videographic representation of anatomy 602 of a patient. In the example of FIG. 6, the anatomy 602 includes the lungs, heart, spine and abdomen. The anatomy 602 can also include, for example, a tumor 603 that is being treated.

The videographic display 600 may be two or three dimensional. In one implementation, the multidimensional data in videographic display 600 can be a combination of the data obtained by the processor 106 from the imaging device 104 and treatment device 102. The two dimensional image data for different orientations of the patient can be obtained by processor 106 from the imaging device 104 and treatment device 102, and this two dimensional data can be combined to form the three dimensional data. The combining may be performed using reconstruction algorithms, such as three-dimensional reconstruction, triangulation, and the like. Some such reconstruction algorithms can involve at least one of: matching pixels in different 2D images, sampling a 3D space, determining a consistency function that correlates (based on variance, covariance, and the like statistical techniques) one or more image parameters (for example, color, anatomical texture, and the like), mapping each pixel in each 2D image to a vector in 3D, and like techniques. When the videographic display 600 has more than two dimensions, a button such as 604 can be provided that can be pressed by a user to view the treatment from different angles; alternatively, a swipe on a touch screen could perform the same function. In one implementation, a user can zoom in or out of the multidimensional display with buttons such as 606 and 608.

Real-time contours enclosing different anatomical structures or other areas such as a region of anatomy targeted for treatment may be included in the videographic display. Contours may be represented in different colors. For example, the display may include a contour 610 around tumor 603, which may red in color while neighboring structures may be enclosed by a blue contour. Various structures may also include internal shading if desired, which may be partially translucent. In the example where the treatment device 102 is a radiation therapy device, the display may include an additional contour 612 representing the location of the planned treatment beam (which typically extends up to some distance outside of the tumor 603).

In one implementation, the videographic display 600 can include an option through which a user can select the contours that the user (for example, a clinician or a user of display 108) may desire to view. For example, if the user desires to view only the contour for the tumor, the user can select just that contour.

Treatment data may be included in videographic display 600. For example, as shown in the FIG. 6 example utilizing a radiation treatment device, beam representations 614 can be included. The beam representations may turn on and off or change shape or angle or intensity as the video progresses, corresponding to the operation of the actual beams during treatment (as determined by the acquired real-time treatment data). The treatment data can be made translucent so that the real-time image data is still visible. This representation of the beams may depict the beams turning on and off in line with the planned treatment regimen, and they may depict turning on and off as a result of the target tumor 603 moving beyond the contour 612 that represents the location of the planned treatment beam (as may occur as a result of patient motion or normal organ motion). The radiation beam treatment data may be depicted in numerous other ways. Another example representation of treatment data includes an indication of accumulated dose deposition. For example, as dose accumulates over the course of the treatment, the region in which the dose is deposited may turn darker in color.

The videographic display 600 may also include an information display 622 for displaying additional data such as a patient identifier (ID), the color of various contours, and additional treatment data. Examples of additional treatment data include total deposited dose, treatment time, beam on time, etc. In some implementations, the amount of dose deposited can vary in real-time as the amount increases during the treatment.

Other treatment data can be included in videographic display 600 when other treatment devices are used. For example, when treatment device 102 is a robotic surgery arm 306 or surgery scalpel 406, a representation of the scalpel or surgery device can be depicted. Alternatively, a representation of where an incision is taking place can be depicted or the representation of treatment data may simply be visible from the imaging data itself. The display may also be configured to depict all or a portion of a medical professional performing the treatment. Numerous other types of treatment data or combinations of treatment data and other data can be depicted. In some implementations, the user can be provided an option to select which set of treatment data the user desires to view and also to select whether or not to depict any other data or even the imaging data.

Although a few implementations have been described in detail above, other modifications are possible. For example, the method depicted in FIG. 5 and described herein may not require the particular order shown, or sequential order, to achieve desirable results.

While various implementations in accordance with the disclosed principles have been described above, it should be understood that they have been presented by way of example only, and are not limiting. Thus, the breadth and scope of the invention(s) should not be limited by any of the above-described exemplary implementations, but should be defined only in accordance with the claims and their equivalents issuing from this disclosure. The present disclosure contemplates that the calculations disclosed in the implementations herein may be performed in a number of ways, applying the same concepts taught herein, and that such calculations are equivalent to the implementations disclosed. Furthermore, the above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A method comprising:
   emitting one or more radiation beams of ionizing radiation from a radiation beam source controlled by a radiation treatment system to a treatment region according to a planned treatment regimen;
   obtaining a plurality of real-time images of the treatment region using an imaging device that is a magnetic resonance imaging system while the radiation beam source emits the one or more radiation beams;
   obtaining real-time treatment data relating to the one or more radiation beams;
   determining one or more real-time contours of relevant anatomy being irradiated in the plurality of the real-time images using an image processing technique; and
   providing for a videographic display of one or more of the plurality of the real-time images, the videographic display including:
   one or more corresponding real-time contours enclosing at least one anatomical structure; and
   one or more beam representations generated based at least on the real-time treatment data relating to the one or more radiation beams, wherein the one or more beam representations depict the one or more radiation beams turning on or off during progression of the videographic display based on the obtained real-time treatment data.

2. The method of claim 1, wherein the image processing technique is deformable image registration.

3. The method of claim 1, wherein the videographic display is provided on a remote device.

4. The method of claim 1, wherein the videographic display is three dimensional.

5. The method of claim 1, wherein the one or more beam representations change angle during progression of the videographic display based on the obtained real-time treatment data.

6. The method of claim 1, wherein the one or more beam representations change shape during progression of the videographic display based on the obtained real-time treatment data.

7. The method of claim 1, wherein the one or more beam representations are translucent so that the videographic display of the one or more of the plurality of the real-time images is visible through the one or more beam representations.

8. A system comprising:
a radiation beam source configured to emit to a treatment region one or more radiation beams of ionizing radiation according to a planned treatment regimen, the radiation beam source further configured to acquire real-time treatment data relating to the one or more radiation beams;
a magnetic resonance imaging system configured to acquire a plurality of real-time images of the treatment region while the one or more radiation beams are emitted from the radiation beam source; and
a processor programmed to determine one or more real-time contours of relevant anatomy being irradiated in the plurality of the real-time images using an image processing technique and to output, to a display, a videographic display of one or more of the plurality of the real-time images, the videographic display including:
one or more corresponding real-time contours enclosing at least one anatomical structure; and
one or more beam representations generated based at least on the real-time treatment data relating to the one or more radiation beams, wherein the one or more beam representations depict the one or more radiation beams turning on or off during progression of the videographic display based on the obtained real-time treatment data.

9. The system of claim 8, wherein the processor is further programmed to implement the image processing technique using deformable image registration.

10. The system of claim 8, wherein the display is on a remote device.

11. The system of claim 8, wherein the processor is further programmed to implement a three dimensional videographic display.

12. The system of claim 8, wherein the processor is further programmed to output a depiction of the one or more beam representations:
changing angle during progression of the videographic display based on the obtained real-time treatment data; or
changing shape during progression of the videographic display based on the obtained real-time treatment data.

13. The system of claim 8, wherein the processor is further programmed to output a depiction of the one or more beam representations being translucent so that the videographic display of the one or more of the plurality of real-time images is visible through the one or more beam representations.

14. A computer program product comprising a non-transitory, machine-readable medium storing instructions which, when executed by at least one programmable processor, cause the at least one programmable processor to perform operations comprising:
obtaining a plurality of real-time images of a treatment region as acquired with an imaging device that is a magnetic resonance imaging system while a radiation beam source emits one or more radiation beams;
obtaining real-time treatment data relating to the one or more radiation beams;
obtaining one or more real-time contours of relevant anatomy being irradiated in the plurality of the real-time images; and
providing for a videographic display of one or more of the plurality of the real-time images, the videographic display including:
one or more corresponding real-time contours enclosing at least one anatomical structure; and
one or more beam representations generated based at least on the real-time treatment data relating to the one or more radiation beams, wherein the one or more beam representations depict the one or more radiation beams turning on or off during progression of the videographic display based on the obtained real-time treatment data.

15. The computer program product of claim 14, the videographic display further including a depiction of the one or more beam representations changing angle during progression of the videographic display based on the obtained real-time treatment data.

16. The computer program product of claim 14, the videographic display further including a depiction of the one or more beam representations changing shape during progression of the videographic display based on the obtained real-time treatment data.

17. The computer program product of claim 14, wherein the videographic display is on a remote device.

18. The computer program product of claim 14, wherein the at least one programmable processor is further programmed to implement a three dimensional videographic display.

19. The computer program product of claim 14, wherein the one or more beam representations are translucent so that the videographic display of the one or more of the plurality of the real-time images is visible through the one or more beam representations.

* * * * *